(12) United States Patent
Honda

(10) Patent No.: US 10,507,030 B2
(45) Date of Patent: Dec. 17, 2019

(54) MEDICAL DEVICE

(71) Applicant: TERUMO KABUSHIKI KAISHA, Shibuya-ku, Tokyo (JP)

(72) Inventor: Kei Honda, Hadano (JP)

(73) Assignee: Terumo Kabushiki Kaisha, Tokyo (JP)

( * ) Notice: Subject to any disclaimer, the term of this patent is extended or adjusted under 35 U.S.C. 154(b) by 234 days.

(21) Appl. No.: 15/068,305

(22) Filed: Mar. 11, 2016

(65) Prior Publication Data

US 2016/0262775 A1 Sep. 15, 2016
US 2017/0367717 A9 Dec. 28, 2017

(30) Foreign Application Priority Data

Mar. 13, 2015 (JP) .................. 2015-050997

(51) Int. Cl.
| | | |
|---|---|---|
| *A61B 17/22* | (2006.01) | |
| *A61M 1/00* | (2006.01) | |
| *A61B 17/00* | (2006.01) | |
| *A61B 90/70* | (2016.01) | |

(52) U.S. Cl.
CPC ........... *A61B 17/22* (2013.01); *A61M 1/0056* (2013.01); *A61B 90/70* (2016.02); *A61B 2017/00473* (2013.01); *A61B 2017/00553* (2013.01); *A61B 2017/22079* (2013.01); *A61B 2217/005* (2013.01)

(58) Field of Classification Search
CPC .......... A61M 1/0056; A61B 90/70; A61B 2017/00553; A61B 2017/00473; A61B 2017/22079; A61B 2217/005
See application file for complete search history.

(56) References Cited

U.S. PATENT DOCUMENTS

| | | | | |
|---|---|---|---|---|
| 5,989,266 A | 11/1999 | Foster | | |
| 6,994,666 B2* | 2/2006 | Shannon | ............ | A61F 2/06 600/16 |
| 2001/0032009 A1* | 10/2001 | Layne | ............ | A61F 2/07 623/1.13 |

(Continued)

FOREIGN PATENT DOCUMENTS

| | | |
|---|---|---|
| JP | 2001-512355 A | 8/2001 |
| WO | WO 98/36694 A1 | 8/1998 |

*Primary Examiner* — Richard G Louis
(74) *Attorney, Agent, or Firm* — Buchanan Ingersoll & Rooney, PC

(57) ABSTRACT

A medical device and method are disclosed, which can sufficiently capture a capturing target even if a lumen is deformed. A medical device has an accommodation unit and an impeller holding unit. The accommodation unit includes a lumen which accommodates a capturing target present inside a living body, in which a shape of at least a portion on a distal side is deformable, and whose inner surface before and after deformation is configured to be flat as a whole, a distal opening portion and a proximal opening portion which respectively communicate with the lumen, and a filter for capturing at least one or more of the capturing targets. The impeller holding unit includes an impeller which causes a fluid to flow from the distal opening portion toward the proximal opening portion inside the living body so as to allow the lumen to aspirate the capturing target together with the fluid.

17 Claims, 8 Drawing Sheets

(56) References Cited

U.S. PATENT DOCUMENTS

| | | | | |
|---|---|---|---|---|
| 2006/0167539 A1* | 7/2006 | McEwan | ............... | A61F 2/01 623/1.35 |
| 2007/0043425 A1* | 2/2007 | Hartley | ............... | A61F 2/07 623/1.12 |
| 2007/0244542 A1* | 10/2007 | Greenan | ............... | A61F 2/07 623/1.13 |
| 2008/0140110 A1* | 6/2008 | Spence | ............... | A61F 2/06 606/200 |

* cited by examiner

MEDICAL DEVICE

CROSS-REFERENCES TO RELATED APPLICATIONS

This application claims priority to Japanese Application No. 2015-050997 filed on Mar. 13, 2015, the entire content of which is incorporated herein by reference.

TECHNICAL FIELD

The present disclosure generally relates to a medical device.

BACKGROUND DISCUSSION

In the related art, treatments have generally been performed in which medical devices such as endoscopes and suction devices are introduced into a biological organ (for example, a body cavity such as an esophagus, airway, intestine, urinary duct, and other organs), and in which these devices are used so as to treat a lesion site appearing in the biological organ, or so as to perform removal of various foreign objects (capturing target) which are present inside the biological organ.

An example of the foreign object can include a calculus formed in the urinary tract. A urinary tract stone is the calculus, which is present in the urinary tract such as the kidney, the urinary duct, the bladder, and the urethra. In case of a urolithiasis, various symptoms are caused to occur due to the urinary tract stone. For example, when the calculus formed inside the kidney moves to the urinary duct, the urinary duct is injured by the calculus, thereby causing pain or hematuria. The calculus occludes the urinary duct, thereby bringing a patient into a transient hydronephrosis state. Consequently, the patient is forced to feel a severe pain (colicky pain) in a range from the waist back to the flank. To remove the calculus is effective means for relieving or treating the symptoms.

In order to remove the calculus, a method has been widely used in which the calculus is picked and extracted by using basket forceps (refer to JP-T-2001-512355). However, it can be necessary to pick the calculus one by one and to extract the calculus from a living body. Consequently, the method can be a very laborious task.

Here, for example, if a method of removing the calculus is tried in such a way that a filter for use in removing a foreign object inside the blood vessel is diverted for the purpose of efficiently extracting the calculus, and that the calculus is accommodated in an accommodation vessel having the filter attached thereto while the calculus aspirated by a fluid is collected in the filter, the above-described problem may be solved.

Furthermore, a size or an amount of the calculus varies depending on a patient. Accordingly, it is preferable to introduce a new technology for treating the patient by adjusting a size of a lumen in an accommodation vessel. However, even when the accommodation vessel is configured to be simply deformable, if unevenness occurs in the lumen of the accommodation vessel, a fluid is disturbed. If the fluid is hindered from flowing in the lumen, it is no longer possible to maintain a suction force required to capture a capturing target. Consequently, there is a possibility that the capturing target cannot be sufficiently captured.

SUMMARY

A medical device is disclosed, which can sufficiently capture a capturing target even if a lumen is deformed.

A medical device according to the present disclosure can include an accommodation unit that includes a lumen which accommodates a capturing target present inside a living body, in which a shape of at least a portion on a distal side is deformable, and whose inner surface before and after deformation is configured to be flat as a whole, a distal opening portion and a proximal opening portion which respectively communicate with the lumen, and a filter for capturing at least one or more of the capturing targets, and an impeller holding unit that includes an impeller which causes a fluid to flow from the distal opening portion toward the proximal opening portion inside the living body so as to allow the lumen to aspirate the capturing target together with the fluid.

According to the medical device, the inner surface of the lumen is flat as a whole before and after deformation. Accordingly, even if the lumen is deformed, there is no possibility of hindering the flow of the fluid, which is formed inside the lumen by the impeller. That is, the medical device can maintain a sufficient suction force in each state before and after the lumen is deformed. Therefore, the medical device can sufficiently aspirate and capture the capturing target even if the lumen is deformed.

A method is disclosed for capturing a target present in a living body, the method comprising: inserting an accommodation unit into the living body, the accommodation unit including a lumen which accommodates a capturing target present inside the living body, in which a shape of at least a portion on a distal side is deformable, and whose inner surface before and after deformation is configured to be flat as a whole, a distal opening portion and a proximal opening portion which respectively communicate with the lumen, and a filter for capturing at least one or more of the capturing targets; and causing a fluid to flow with an impeller holding unit, the impeller holding unit including an impeller which causes the fluid to flow from the distal opening portion toward the proximal opening portion inside the living body so as to allow the lumen to aspirate the capturing target together with the fluid.

BRIEF DESCRIPTION OF THE DRAWINGS

FIGS. 8A-8C are perspective views schematically illustrating a state where a capturing target is collected in an accommodation unit of the medical device in FIG. 1, wherein FIG. 8A is a view illustrating a state before the capturing target is collected in the accommodation unit, FIG.

8B is a view illustrating a state while the capturing target is collected in the accommodation unit, and FIG. 8C is a view illustrating a state after the capturing target is collected in the accommodation unit.

DETAILED DESCRIPTION

Figure 1:
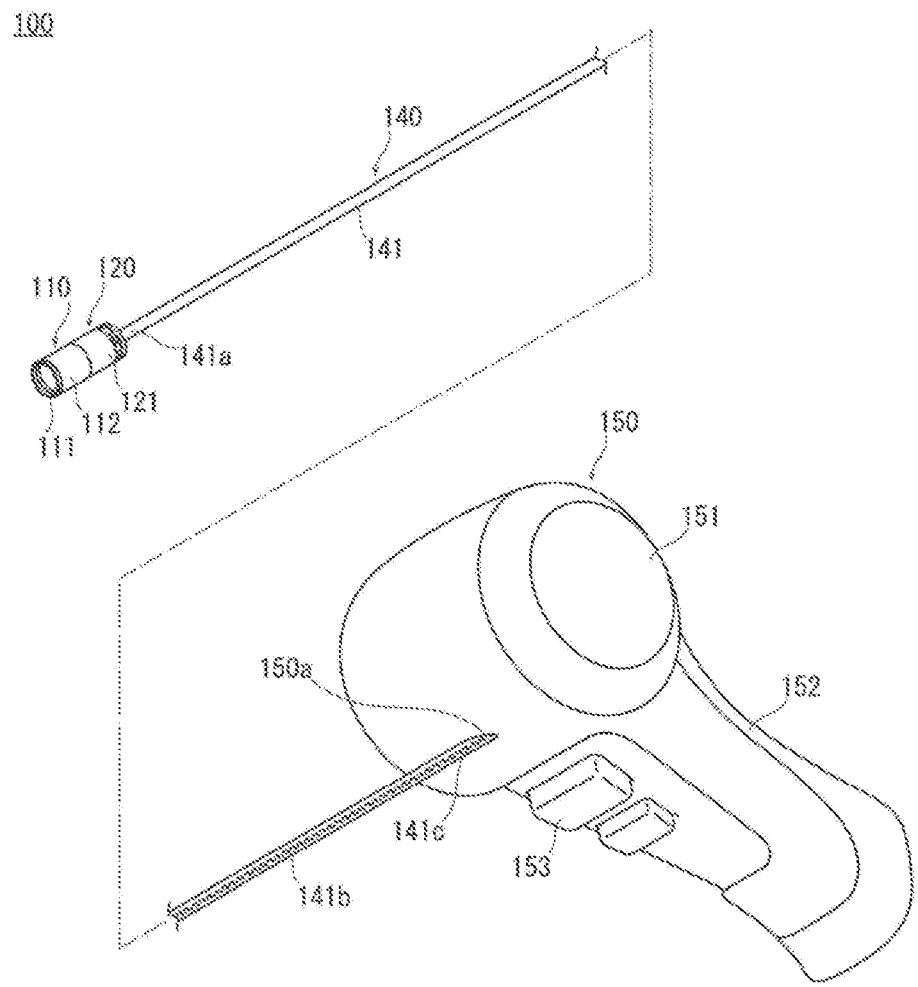
FIG. 1 is a perspective view illustrating a medical device according to a first embodiment.

Hereinafter, embodiments of the present disclosure will be described with reference to the drawings. In some cases, dimensional proportions in the drawings may be exaggerated and different from actual proportions for convenience of description. In a medical device 100, an accommodation unit 110 side which is introduced into a living body corresponds to a distal side, and a hand operation unit 150 operated by a user (operator) corresponds to a proximal side.

The medical device 100 according to a first embodiment will be described with reference to FIGS. 1 to 8C.

A configuration of the medical device 100 will be described with reference to FIGS. 1 to 5.

In accordance with an exemplary embodiment, the medical device 100 can sufficiently capture a capturing target even if a lumen 110b is deformed in accordance with an internal shape of a living body (for example, a urinary duct 630) which varies depending on a patient, a size or an amount of the capturing target (for example, a solid calculus K or a semi-solid blood clot B) which is present inside the living body. As for the capturing target, the calculus K can include calculus fragments obtained by fragmenting the calculus K present in the urinary duct 630 by using a laser lithotripsy device, for example, and by relatively decreasing the size thereof. An accommodation unit 110, an impeller holding unit 120, an introduction unit 140, and a hand operation unit 150 which configure the medical device 100 will be sequentially described.

As illustrated in FIGS. 1 to 5, the accommodation unit 110 accommodates the capturing target which is present inside the living body such as the urinary duct 630.

The accommodation unit 110 can include a first cylinder 111, an expandable member 112, and a filter 113. The first cylinder 111 and the expandable member 112 respectively have a cylindrical shape, and can be joined to each other in a state where both of these are adjacent to each other along the axial direction. The accommodation unit 110 can include a distal opening portion 110a on the distal side (upstream side along the axial direction) of the first cylinder 111. For example, the distal opening portion 110a is formed in a circular shape in a cross section orthogonal to the axis. The accommodation unit 110 can include a proximal opening portion 110c on the proximal side (downstream side along the axial direction) of the expandable member 112. For example, the proximal opening portion 110c is formed in a circular shape in a cross section orthogonal to the axis. The accommodation unit 110 integrally can include the lumen 110b for accommodating the capturing target, inward from the first cylinder 111 and the expandable member 112. The accommodation unit 110 can include the filter 113 at a position which is located on the proximal side (downstream side along the axial direction) of the expandable member 112 and which faces the proximal opening portion 110c.

While maintaining a shape in a cross section orthogonal to the axis of the expandable member 112, the first cylinder 111 protects the expandable member 112 when being introduced into the living body with the accommodation unit 110 at the head. The first cylinder 111 has a cylindrical shape, and is formed so that the thickness is sufficiently thinner compared to the diameter. The proximal side along the axial direction of the first cylinder 111 is joined to the distal side along the axial direction of the expandable member 112. In the first cylinder 111, the length along the axial direction is sufficiently shorter compared to the diameter. In accordance with an exemplary embodiment, the first cylinder 111 is not essential as long as the expandable member 112 has a sufficiently fixed form.

For example, the first cylinder 111 can be configured to include a rigid material formed of polyolefin, such as acrylic resin, polyvinyl chloride (particularly, rigid polyvinyl chloride), polyethylene, polypropylene, or polybutadiene. In addition, for example, the first cylinder 111 is configured to include a flexible material, and can be configured to be deformable along a shape of, for example, the urinary duct 630. The first cylinder 111 is configured to include a material, which is transparent in a visible light region, and can be configured so that capturing progress of the capturing target is visible from the outside. For example, the first cylinder 111 can be configured to include an X-ray contrast agent. The contrast agent is imaged from the outside by using X-ray fluoroscopy. In this manner, a position of the first cylinder 111 inside the living body can be confirmed.

The expandable member 112 expands or contracts, thereby enabling the lumen 110b of the accommodation unit 110 to be increased or decreased in volume. The distal side along the axial direction of the expandable member 112 is joined to the proximal side along the axial direction of the first cylinder 111. The expandable member 112 has a cylindrical shape, and is formed so as to be alternately folded radially inward and radially outward along the axial direction. That is, the expandable member 112 is formed in a bellows shape.

Figure 2:
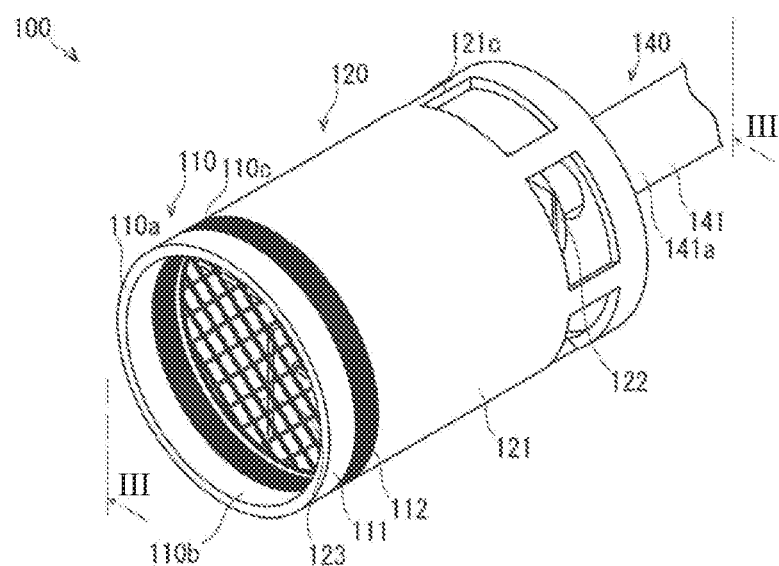
FIG. 2 is a perspective view illustrating a main unit of the medical device in FIG. 1 in a state where a first cylinder is contracted.
Figure 3:
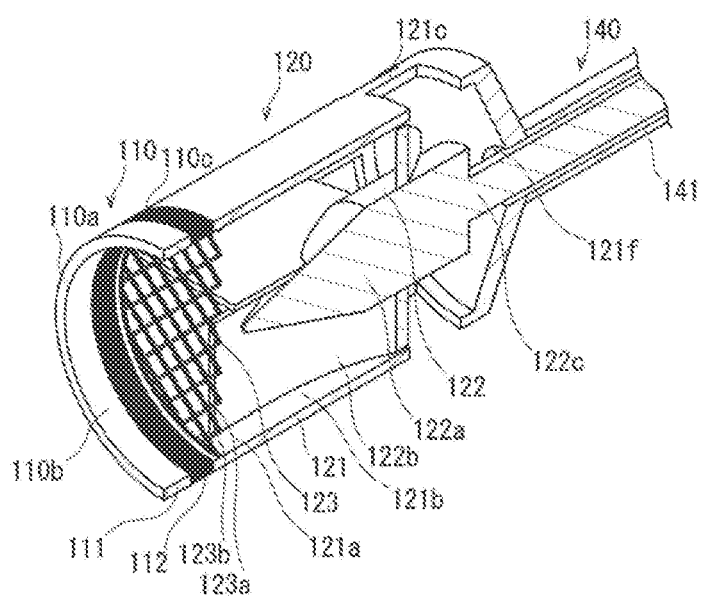
FIG. 3 is a perspective view illustrating the main unit of the medical device in FIG. 1 by using a cross section taken along line III-III in FIG. 2.

When being contracted, the expandable member 112 is configured so that the length along the axial direction is considerably shortened compared to the diameter, as illustrated in FIGS. 2 and 3. When being contracted, the expandable member 112 is configured so that the inner surface is smooth as a whole, since the expandable member 112 has the bellows shape and folded portions are in close contact with each other. As illustrated in FIG. 3, when being contracted, the first cylinder 111 is configured so that the thickness is sufficiently thinner compared to the diameter.

Figure 4:
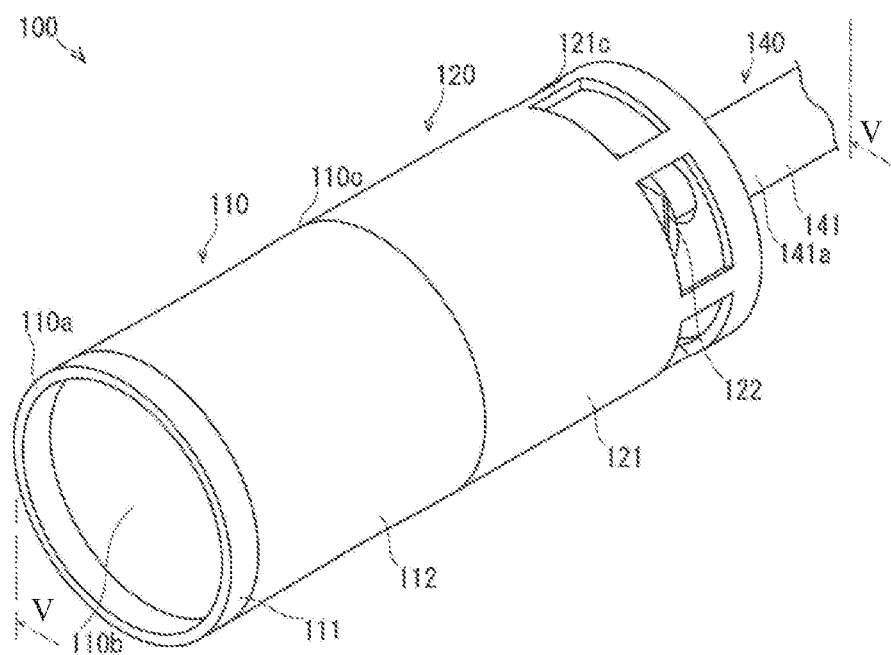
FIG. 4 is a perspective view illustrating the main unit of the medical device in FIG. 1 in a state where a first cylinder is expanded.
Figure 5:
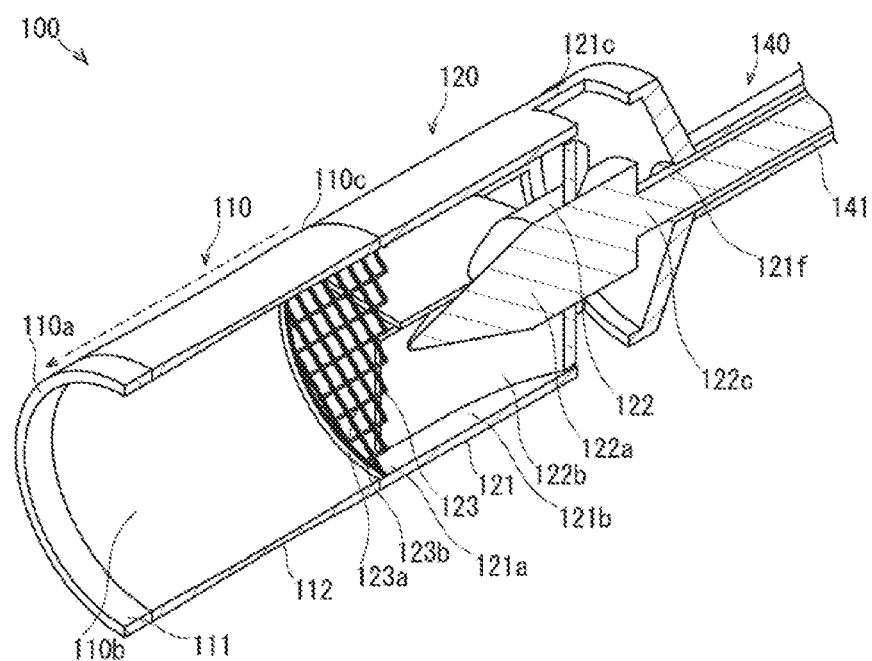
FIG. 5 is a perspective view illustrating the main unit of the medical device in FIG. 1 by using a cross section taken along line V-V in FIG. 4.

In accordance with an exemplary embodiment, when being expanded, the expandable member 112 is configured so that the length along the axial direction is considerably lengthened compared to the diameter, as illustrated in FIGS. 4 and 5. When being expanded, the expandable member 112 is configured so that the inner surface is smooth as a whole, since the expandable member 112 has the bellows shape and the folded portions are stretched.

For example, the expandable member 112 can be configured to include a flexible soft material such as polyvinyl chloride and polyethylene. Similarly to the first cylinder 111, the expandable member 112 can be configured to include a material which is transparent in a visible light region, or can be configured to include an X-ray contrast agent.

The filter 113 is used in order to capture a capturing target. The filter 113 adopts a configuration which allows a fluid to pass therethrough and does not allow the capturing target having the solid calculus K or the semi-solid blood clot B to pass therethrough, for example. That is, the filter 113 can distinguish the capturing target from the fluid, and can capture the capturing target which moves together with the fluid from the distal opening portion 110a of the accommodation unit 110 toward the distal opening portion 121a of the second cylinder 121. For example, the filter 113 is joined at a position which is located on the proximal side of the lumen 110b of the first cylinder 111 and which faces the proximal opening portion 110c.

The filter 113 can include a holding portion 113a and a frame portion 113b. The holding portion 113a holds the capturing target. The holding portion 113a is formed in a lattice shape. The holding portion 113a is arranged so that the main surface is perpendicular to the axial direction inside the lumen 110b. The frame portion 113b supports the holding portion 113a along the circumferential direction. The frame portion 113b is formed in a ring shape, and is formed integrally in an outer periphery edge of the holding portion 113a.

For example, the filter 113 can be configured by using a woven fabric formed of woven stuff or knitted fabric, a fibrous material formed of mesh fabric having a predetermined mesh such as non-woven fabric and the like, a porous film, or the like. In particular, the mesh fabric has a relatively uniform mesh. Accordingly, the mesh fabric can suitably configure the filter 113. The filter 113 may be configured to include a combination of the above-described multiple materials.

As illustrated in FIGS. 1 to 5, the impeller holding unit 120 causes a fluid to flow from the distal opening portion 110a toward the proximal opening portion 110c in the urinary duct 630 and the like.

The impeller holding unit 120 is configured to be detachably attached or joined to the accommodation unit 110 on the proximal side of the accommodation unit 110. The impeller holding unit 120 can include the second cylinder 121 and an impeller 122. The second cylinder 121 is formed in a cylindrical shape, and accommodates the impeller 122 so as to be rotatable. The second cylinder 121 can include a distal opening portion 121a through which a fluid is caused to flow from the first cylinder 111 on a distal side (upstream side along the axial direction) of a lumen 121b. For example, the distal opening portion 121a is formed in a circular shape in a cross section orthogonal to the axis. The distal opening portion 121a of the second cylinder 121 is joined to the proximal opening portion 110c of the first cylinder 111, for example.

The second cylinder 121 can include a proximal opening portion 121c through which the fluid is caused to flow (discharged) on a side surface on a proximal side (downstream side along the axial direction) of the lumen 121b. The proximal opening portion 121c is formed at multiple locations at a constant interval along a circumferential direction on the proximal side of the second cylinder 121. The proximal opening portion 121c is formed in a rectangular shape along the circumferential direction of the second cylinder 121. In the second cylinder 121, a support hole 121f into which an axle portion 122c of the impeller 122 is rotatably inserted for support is formed in the center of the proximal side end portion of the lumen 121b.

Similarly to the first cylinder 111, the second cylinder 121 can be configured to include a rigid material formed of polyolefin, such as acrylic resin, polyvinyl chloride (particularly, rigid polyvinyl chloride), polyethylene, polypropylene, or polybutadiene. Similarly to the first cylinder 111, the second cylinder 121 can be configured to include a material which is transparent in a visible light region, or can be configured to include an X-ray contrast agent.

The impeller 122 causes a fluid to flow from the distal opening portion 110a toward the proximal opening portion 110c, and causes the accommodation unit to aspirate the capturing target together with the fluid. The impeller 122 is rotatably accommodated inside the second cylinder 121. The impeller 122 can include a shaft portion 122a, multiple blade portions 122b, and the axle portion 122c. The impeller 122 configures a propeller-type screw as a whole by using the shaft portion 122a and the multiple blade portions 122b.

Along the axial direction, the shaft portion 122a rotates the blade portion 122b which is joined at multiple locations at a constant interval along the circumferential direction. The shaft portion 122a is a columnar body whose diameter on the distal side (upstream side along the axial direction) is reduced, and has a bullet shape as a whole. The elongated and elastic axle portion 122c is interlocked with the proximal side end portion (downstream side along the axial direction) of the blade portion 122b. The axle portion 122c is connected to a motor of a control member 151 of the hand operation unit 150.

The blade portion 122b corresponds to a screw blade portion. If the blade portion 122b is rotated by the shaft portion 122a, a fluid is caused to flow from the distal opening portion 121a of the second cylinder 121 toward the proximal opening portion 121c. The distal opening portion 121a of the second cylinder 121 is interlocked with the proximal opening portion 110c of the first cylinder 111. That is, while the blade portion 122b is rotated, the fluid is caused to flow from the distal opening portion 110a of the accommodation unit 110 toward the proximal opening portion 121c of the second cylinder 121.

In the blade portion 122b, the length along the axial direction is longer than the length along a radial direction. In the blade portion 122b, the width along the radial direction is the same as the width along the axial direction, and is formed in a so-called square shape. The blade portion 122b is longitudinally twisted from the distal side to the proximal side based on a rotation axis so that the rotation of the shaft portion 122a enables a fluid to flow. Furthermore, the blade portion 122b is curved radially outward from the rotation axis in a direction opposite to the rotation direction.

Except for the axle portion 122c, for example, the impeller 122 can be configured to include a rigid resin material formed of polyolefin, such as acrylic resin, polyvinyl chloride (particularly, rigid polyvinyl chloride), polyethylene, polypropylene, or polybutadiene. In addition, except for the axle portion 122c, for example, the impeller 122 can be configured to include a metal material, which is a pseudo-elastic alloy (including a super-elastic alloy) such as a Ni—Ti alloy, a shape memory alloy, stainless steel, a cobalt-based alloy, precious metal such as gold and platinum, a tungsten-based alloy, or a carbon-based material (including piano wire). The axle portion 122c can be configured to include a flexible material.

As illustrated in FIGS. 1 to 5, the introduction unit 140 is used by an operator in order to introduce the accommodation unit 110 and the impeller holding unit 120 into the living body such as the urinary duct 630.

The introduction unit 140 can include an introduction tube 141. The introduction tube 141 is formed in an elongated cylinder shape. A lumen 141b which can rotatably hold the axle portion 122c of the impeller 122 is formed inside the introduction tube 141. A distal end 141a of the introduction tube 141 is joined to the support hole 121f of the second cylinder 121 of the impeller holding unit 120. A proximal end 141c of the introduction tube 141 is connected to a connection port 150a of the hand operation unit 150 so as to be attachable and detachable. The introduction tube 141 is configured to include a flexible material, and can be deformed in accordance with a shape of, for example, the urinary duct 630, or the movement of the flexible scope 700.

As illustrated in FIG. 1, the hand operation unit 150 is operated by an operator in order to adjust a position of the first cylinder 111 introduced into the urinary duct 630, or in order to rotate the impeller 122.

The hand operation unit 150 can include the control member 151, a gripping member 152, and a switch 153. The hand operation unit 150 can include a connection port 150a for connecting the proximal end 141c of the introduction tube 141 of the introduction unit 140 so as to be attachable and detachable. The control member 151 can include a motor for rotating the axle portion 122c of the impeller 122, a control circuit for controlling the motor, and a power source (battery) for supplying power to the motor and the control circuit. A rotary shaft of the motor is interlocked with the axle portion 122c of the impeller 122 so as to be attachable and detachable. If the motor of the control member 151 is rotated, the axle portion 122c of the impeller 122 introduced into the introduction tube 141 is rotatably driven, thereby rotating the impeller 122 inside the second cylinder 121. The gripping member 152 is gripped by an operator. The gripping member 152 internally stores a battery of the control member 151. The switch 153 turns on and off the motor of the control member 151.

A method of using the medical device 100 will be described with reference to FIGS. 6 to 8C.

Figure 6:
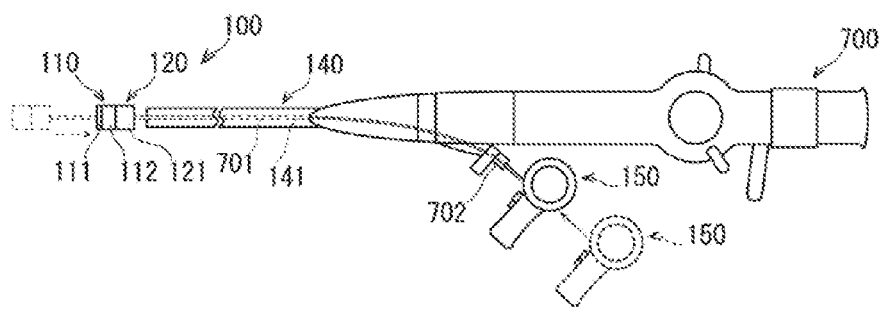
FIG. 6 is a side view schematically illustrating a state where the medical device in FIG. 1 is mounted on a flexible pyeloscope (hereinafter, referred to as a flexible scope).
Figure 7:
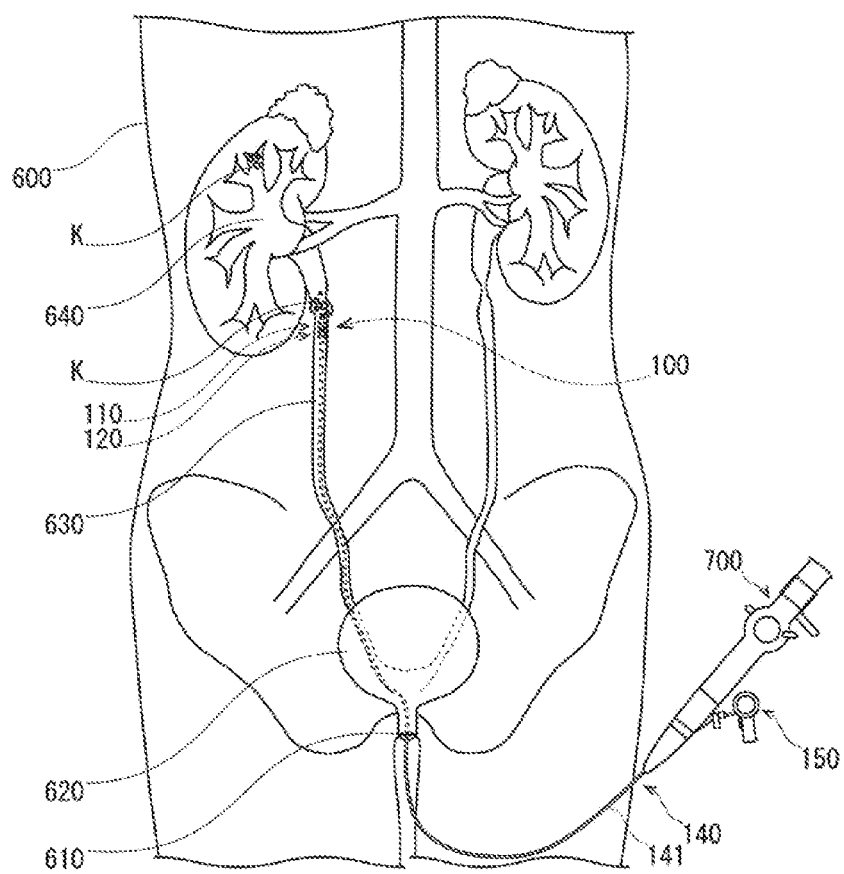
FIG. 7 is a view schematically illustrating a state where the flexible scope on which the medical device in FIG. 1 is mounted is introduced into a patient's urinary duct.
Figure 8A:
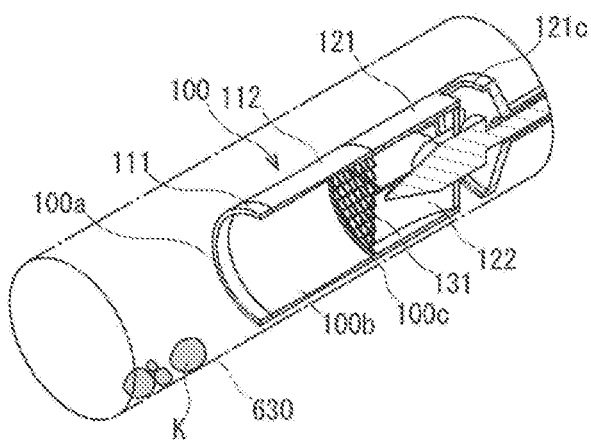
Figure 8B:
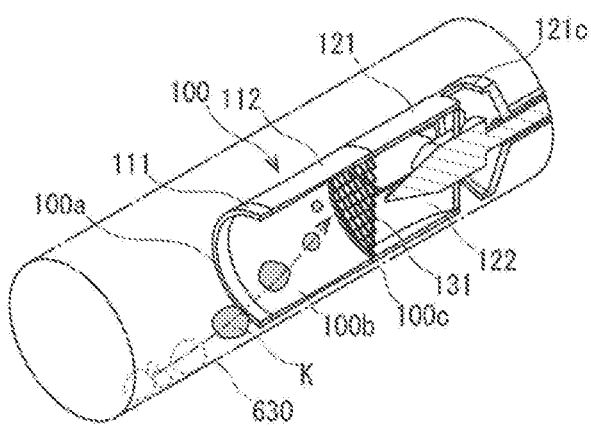
Figure 8C:
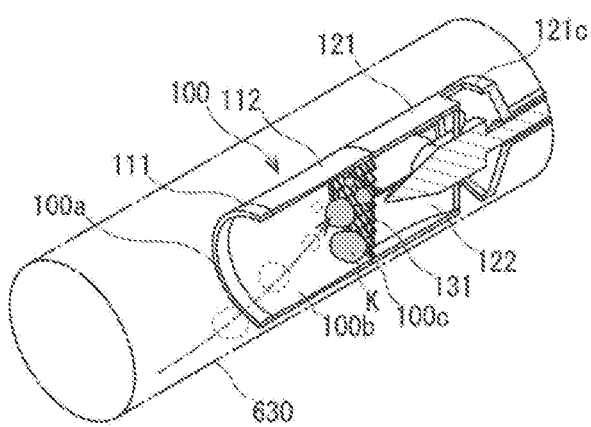

FIG. 6 is a side view schematically illustrating a state where the medical device 100 illustrated in FIG. 1 is mounted on a flexible pyeloscope (hereinafter, referred to as a flexible scope). FIG. 7 is a view schematically illustrating a state where the flexible scope on which the medical device 100 illustrated in FIG. 1 is mounted is introduced into a patient's urinary duct. FIGS. 8A-8C are perspective views schematically illustrating a state where a capturing target is collected in the accommodation unit 110 of the medical device 100 illustrated in FIG. 1. FIG. 8A is a view illustrating a state before the capturing target is collected in the accommodation unit 110, FIG. 8B is a view illustrating a state while the capturing target is collected in the accommodation unit 110, and FIG. 8C is a view illustrating a state after the capturing target is collected in the accommodation unit 110.

In the description relating to the method of using the medical device 100, the capturing target will be described as the calculus K, for example.

Hereinafter, a patient 600 who suffers from the urolithiasis will be described by citing a case where the patient 600 has the calculus K present in a region corresponding to a lower urinary duct which is reachable by a rigid scope of the urinary duct 630, and also has the calculus K in a region corresponding to an upper urinary duct which is less likely to be reachable by the rigid scope of the urinary duct 630 but is reachable by the flexible scope. In this case of disease, the calculus K in the lower urinary duct is first removed, and then the calculus K in the upper urinary duct is removed. FIG. 7 schematically illustrates a situation when the calculus K in the upper urinary duct is removed after the calculus K in the lower urinary duct is removed.

In order to treat the patient 600 illustrated in FIG. 7, a cystoscope generally used in the urinary system is used so as to introduce a guidewire widely known in the medical field into the urinary duct 630 or a renal pelvis and renal calyx 640 via a urethra 610 and a bladder 620. Next, a rigid pyeloscope (hereinafter, referred to as a rigid scope) is inserted so as to observe an inner wall of the urinary duct 630 or the calculus K inside the urinary duct 630. In this case, the calculus K may be removed by using the rigid scope in combination with basket forceps. In addition, the rigid scope may be used in combination with a fragmenting device such as a holmium YAG laser and the like so as to fragment the relatively big calculus K which is less likely to be removed into relatively smaller fragments. Alternatively, the generated calculus fragments may be removed by using the basket forceps. Thereafter, the rigid scope is removed from the inside of the living body.

Next, a ureteral access sheath is introduced into the urinary duct 630 or the renal pelvis and renal calyx 640 via the urethra 610 and the bladder 620 through the guidewire.

The flexible scope 700 is inserted via the ureteral access sheath so as to observe the calculus K. In this case, the guidewire may be removed. When the calculus K has a relatively large size, which is less likely to pass through the ureteral access sheath, the flexible scope 700 is used in combination with the fragmenting device such as, for example, the holmium YAG laser so as to fragment the calculus K into a relatively small size.

Next, the medical device 100 and the flexible scope 700 are assembled to each other. Specifically, as illustrated in FIG. 6, in a state where the introduction tube 141 and the hand operation unit 150 in the medical device 100 are separated from each other, the introduction tube 141 is introduced into a working channel 701 of the flexible scope 700 from the distal side of the flexible scope 700. The proximal side of the introduction tube 141 is extracted from a port 702, and the proximal side of the introduction tube 141 is fitted and attached to the hand operation unit 150.

Next, as illustrated in FIG. 7, the flexible scope 700 having the medical device 100 mounted thereon is caused to pass through the urethra 610 and the bladder 620 of the patient 600 via the ureteral access sheath, and is caused to reach a site having the calculus K present inside the urinary duct 630, for example. Thereafter, the calculus K is collected in the accommodation unit 110 by using the medical device 100.

Specifically, as illustrated in FIG. 8A, the first cylinder 111 is caused to move close to the calculus K inside the urinary duct 630 illustrated in FIG. 7. If an operator operates the switch 153 of the hand operation unit 150 so as to rotate the impeller 122, a fluid is caused to flow from the distal opening portion 110a of the accommodation unit 110 toward the proximal opening portion 121c of the second cylinder 121. As a result, as illustrated in FIGS. 8B to 8C, the calculus K inside the urinary duct 630 is moved and captured while being attracted to the filter 113 arranged in the first cylinder 111. The calculus K captured by the filter 113 is accommodated in the first cylinder 111.

According to the medical device 100, the expandable member 112 is expanded, and a volume inside the lumen 110b is increased. In this manner, compared to a state before the expandable member 112 is expanded, the medical device 100 can accommodate more calculi into the lumen 110b. Here, according to the medical device 100, the inner surface of the lumen 110b is flat as a whole after being deformed (after being expanded). Accordingly, the fluid is not hindered from flowing by the lumen 110b, and there is no turbulent flow. That is, the medical device 100 can maintain a sufficient suction force in a state after the lumen 110*b* is deformed. Therefore, the medical device 100 can sufficiently capture the calculus K.

In accordance with an exemplary embodiment, according to the medical device 100, if the calculus can be sufficiently accommodated (case where there are very few calculi K to be removed) even when the expandable member 112 is contracted and the volume inside the lumen 110*b* is decreased, the lumen 110*b* is deformed so as to be contracted, thereby enabling the lumen 110*b* to be smoothly introduced into the living body and to be smoothly extracted from the living body. Here, according to the medical device 100, as illustrated in FIGS. 2 and 3, the inner surface of the lumen 110*b* is flat as a whole after being deformed (after being contracted). Accordingly, the fluid is not hindered from flowing by the lumen 110*b*, and there is no turbulent flow. That is, the medical device 100 can maintain a sufficient suction force even in a state after the lumen 110*b* is deformed so as to be contracted. Therefore, the medical device 100 can sufficiently capture the calculus K.

Next, the first cylinder 111 or the like which collects the calculus K in the first cylinder 111 is conveyed to the outside of the body in a state where a suction force is generated. The first cylinder 111 is detached from the second cylinder 121 and the calculus K inside the first cylinder 111 is removed. Thereafter, the first cylinder 111 is attached to the second cylinder 121 again. Alternatively, a new first cylinder 111 is attached to the second cylinder 121. The calculus K inside the first cylinder 111 may be removed outside the body in a state where the first cylinder 111 is joined to the second cylinder 121, by using the medical device 100 in which the first cylinder 111 is joined to the second cylinder 121.

Then, the accommodation unit 110 of the medical device 100 is caused to reach the site having the calculus K again. Thereafter, the calculus K is repeatedly aspirated into the first cylinder 111, and is repeatedly removed outside the body. Furthermore, in order to change a position of (reposition) the calculus K, the medical device 100 may be controlled so that the calculus K is aspirated into the first cylinder 111 in a renal calyx located inside the renal pelvis and renal calyx, and so that the rotation of the motor is minimized or stopped in the other renal calyx. In this manner, the calculus K may be released from the first cylinder 111. In this case, an operation may be performed so as to discharge the calculus K from the first cylinder 111 by reversely rotating the motor.

The medical device 100 may be used together with the rigid scope. That is, instead of the basket forceps, the rigid scope may be used for observing, fragmenting, and extracting operations which are performed before the extracting operation is performed by using the flexible scope 700.

Next, the guidewire is introduced into the urinary duct 630 or the renal pelvis and renal calyx 640 via the urethra 610 and the bladder 620. This operation may be performed via the ureteral access sheath. Furthermore, a ureteral stent for upper urinary duct indwelling is caused to indwell while covering the guide wire, and thereafter the guidewire is removed. The ureteral stent corresponds to a transient ureteral obstruction after operation. After a predetermined number of days elapses, the ureteral stent is removed.

Whether to use the ureteral access sheath or not is determined by an operator in view of conditions of the urinary duct 630 or the calculus K. That is, without using the ureteral access sheath, observing, fragmenting, and extracting operations may be performed by using the flexible scope 700. Even in this case, the medical device 100 may be used together with the flexible scope 700.

The manual skills described with reference to FIGS. 6 to 8C are mainly as follows. According to a method of removing the capturing target captured by the medical device 100 introduced into the living body of the patient 600, the lumen 110*b* is deformed in accordance with the inside of the living body or the capturing target, and the medical device 100 is introduced into the living body so as to capture the capturing target. Thereafter, the medical device 100 is extracted from the living body, and the capturing target is removed.

As described above, according to the medical device 100 of the first embodiment, the following configurations provide an operation effect.

According to the medical device 100, the inner surface of the lumen 110*b* is flat as a whole before and after deformation. Accordingly, even if the lumen 110*b* is deformed, there is no possibility of hindering flow of the fluid, which is formed inside the lumen 110*b* by the impeller 122. That is, the medical device 100 can maintain a sufficient suction force in each state before and after the lumen 110*b* is deformed. Therefore, the medical device 100 can sufficiently capture the capturing target even if the lumen 110*b* is deformed.

Furthermore, according to the medical device 100, the accommodation unit 110 can include the deformable section configured to be expandable and/or bendable along the axial direction in which the fluid flows. According to this configuration, the medical device 100 can increase or decrease the volume inside the lumen 110*b* by expanding or contracting the expandable member 112 in accordance with an amount of the capturing target. Therefore, after the accommodation unit 110 optionally deforms in accordance with the amount of the capturing target, the medical device 100 can sufficiently aspirate and capture the capturing target.

In addition, according to the medical device 100, the accommodation unit 110 can include the deformable section configured to be expandable and/or bendable along the axial direction in which the fluid flows. According to this configuration, the medical device 100 can expand, contract, or bend the accommodation unit 110 along the axial direction in accordance with an internal shape of the living body. Therefore, after the accommodation unit 110 optionally deforms in accordance with the internal shape of the living body, the medical device 100 can sufficiently aspirate and capture the capturing target.

Furthermore, according to the medical device 100, the deformable section can include the expandable member 112, which has a tubular shape along the axial direction in which the fluid flows, and at least a portion of which is formed in a bellows shape so as to be expandable. According to this configuration, since the accommodation unit 110 can be conveniently deformed, the medical device 100 can sufficiently capture the capturing target. In particular, according to this configuration, it is possible to obtain a desired deformation amount (for example, the length along the axial direction) by appropriately setting specifications of the expandable member 112. Furthermore, according to this configuration, the expandable member 112 can be expanded and bent along the axial direction. Therefore, the expandable member 112 can be accurately deformed in accordance with the internal shape of the living body.

A medical device 200 according to a second embodiment will be described with reference to FIGS. 9 and 10. According to the medical device 200, a configuration in which an accommodation unit 210 can include a bending member 211, which is bendable and a winding member 212 which is wound in a spiral shape radially outward from the bending member 211 is different from the configuration of the medical device 100 according to the above-described first embodiment. In the second embodiment, the same reference numerals are given to the same configuration elements as those in the above-described first embodiment, and repeated description will be omitted.

A configuration of the medical device 200 according to the second embodiment will be described with reference to FIGS. 9 to 10.

Figure 9:
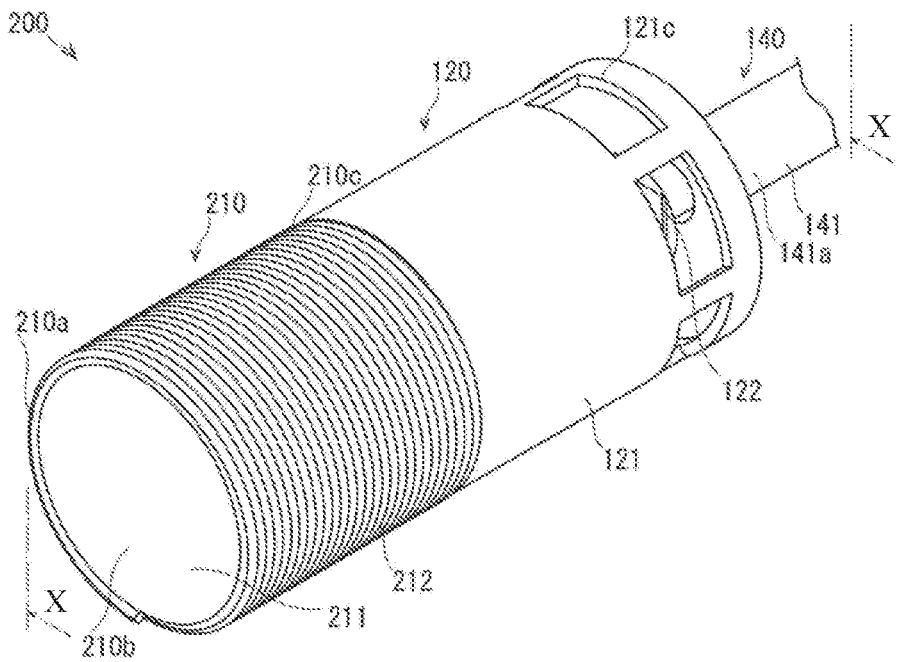
FIG. 9 is a perspective view illustrating a main unit of a medical device according to a second embodiment.
Figure 10:
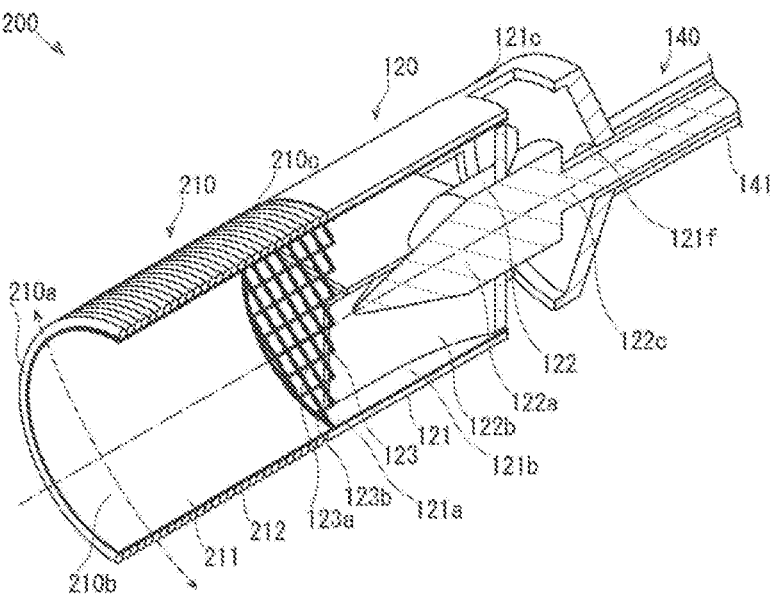
FIG. 10 is a perspective view illustrating the main unit of the medical device in FIG. 9 by using a cross section taken along line X-X in FIG. 9.

FIG. 9 is a perspective view illustrating a main unit of the medical device 200 according to the second embodiment. FIG. 10 is a perspective view illustrating the main unit of the medical device 200 in FIG. 9 by using a cross section taken along line X-X in FIG. 9.

The accommodation unit 210 can include the bending member 211 and the winding member 212. The bending member 211 and the winding member 212 respectively have a cylindrical shape, and are joined to each other in a state where both of these are adjacent to each other along the radial direction. The bending member 211 is arranged inward from the winding member 212. The accommodation unit 210 can include a distal opening portion 210a on the distal side (upstream side along the axial direction) of the bending member 211 and the winding member 212. For example, the distal opening portion 210a is formed in a circular shape in a cross section orthogonal to the axis. The accommodation unit 210 can include a proximal opening portion 210c on the proximal side (downstream side along the axial direction) of the bending member 211 and the winding member 212. For example, the proximal opening portion 210c is formed in a circular shape in a cross section orthogonal to the axis. The accommodation unit 210 can include a lumen 210b for accommodating a capturing target, inward from the bending member 211.

The bending member 211 has a tubular shape along the axial direction in which a fluid flows, and at least a portion is flexible and bendable. The bending member 211 is configured so that an inner surface of the lumen 210b of the accommodation unit 210 is smooth as a whole. The bending member 211 has a cylindrical shape, and the thickness is formed to be much thinner compared to the diameter.

The winding member 212 is wound in a spiral shape along the axial direction in which the fluid flows, radially outward from the bending member 211. For example, the winding member 212 configures a coil obtained by winding a wire formed of hard plastic or metal into a spiral shape. The winding member 212 supports the bending member 211, which is bonded inward, and holds the bending member 211 so that the inner surface is smooth as a whole. A shape of the winding member 212 (for example, a convex shape formed in a gap between coils) does not affect the bending member 211. That is, the winding member 212 supports the bending member 211, and partially (spirally) supports an outer surface of the bending member 211 without coming into close contact with the entire outer surface of the bending member 211. Accordingly, the winding member 212 does not bend or distort the bending member 211. For example, if the bending member 211 receives pressure inside the living body, the bending member 211 deforms itself so as to be bent.

As described above, according to the medical device 200 of the second embodiment, the following configurations provide an operation effect.

According to the medical device 200, the deformable section can include the bending member 211 and the winding member 212. The bending member 211 has a tubular shape along the axial direction in which the fluid flows, and at least a portion is flexible and bendable. The winding member 212 is wound in a spiral shape along the axial direction in which the fluid flows, radially outward or inward from the bending member 211. According to this configuration, in the medical device 200, the bending member 211 can be bent into various shapes while the inner surface of the lumen 210b of the accommodation unit 210 is configured to be smooth as a whole, and the shape of the bending member 211 can be held by the winding member 212. That is, the medical device 200 can maintain a sufficient suction force in each state before and after the lumen 210b is deformed. Therefore, the medical device 200 can sufficiently capture the capturing target even if the lumen 210b is deformed.

Furthermore, for example, when the winding member 212 is pressed against the urinary duct 630 or the renal pelvis and renal calyx 640, the winding member 212 can bend itself so as to be deformed. In addition, if the winding member 212 is separated from the urinary duct 630 or the renal pelvis and renal calyx 640, the winding member 212 can restore its own initial shape. Furthermore, for example, when there is a narrow entrance to a tissue lumen such as a lower calyx and the like inside the living body and the winding member 212 is pressed against a curved site, the winding member 212 can be deformed along the shape of the tissues. Accordingly, it becomes relatively easy to insert the distal opening portion 210a of the medical device 200 into the lower calyx, for example.

In accordance with an exemplary embodiment, for example, when the winding member 212 is arranged by being wound radially outward from the bending member 211, the bending member 211 can cause the inner surface of the lumen 210b to be flat as a whole before and after the deformation, without depending on the spiral shape of the winding member 212.

A medical device 300 according to a third embodiment will be described with reference to FIGS. 11 and 12. According to the medical device 300, a configuration in which an accommodation unit 310 can include a first deformable member (first cylinder 311) and a second deformable member (second cylinder 312) which are screwed to each other and which can change the entire length is different from each configuration of the medical devices 100 and 200 according to the above-described first and second embodiments. In the third embodiment, the same reference numerals are given to the same configuration elements as those in any one of the above-described first and second embodiments, and repeated description will be omitted.

A configuration of the medical device 300 according to the third embodiment will be described with reference to FIGS. 11 and 12.

Figure 11:
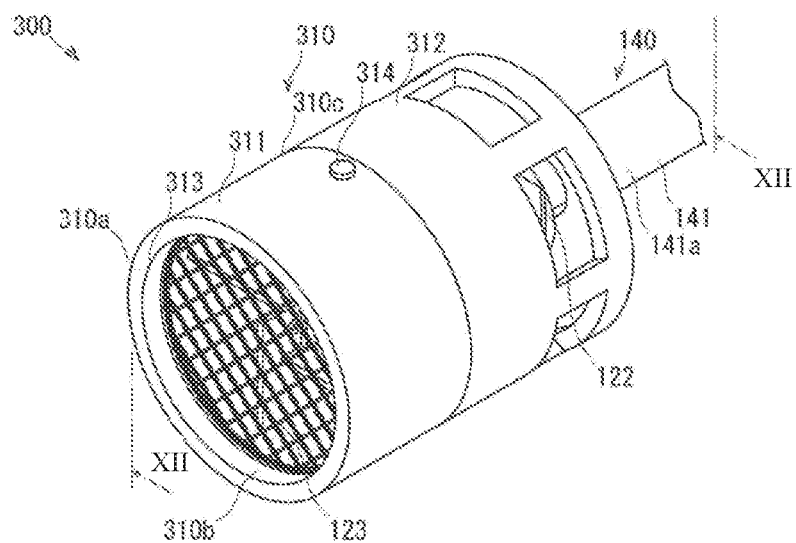
FIG. 11 is a perspective view illustrating a main unit of a medical device according to a third embodiment.
Figure 12:
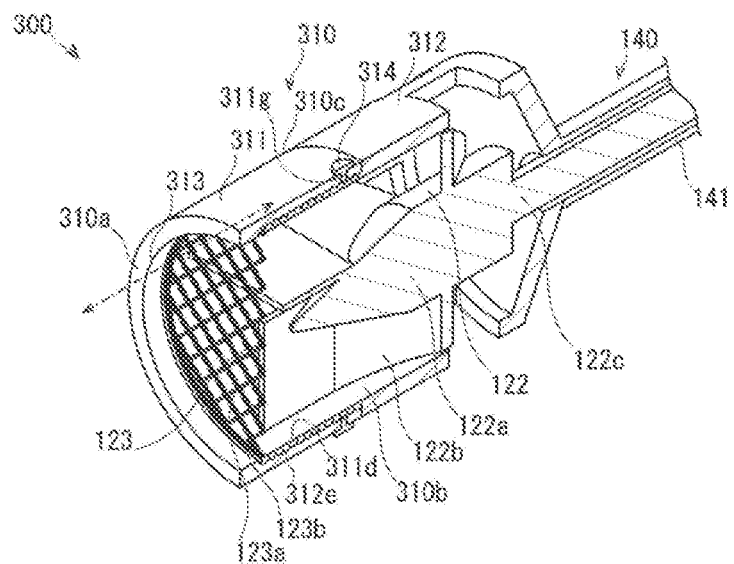
FIG. 12 is a perspective view illustrating the main unit of the medical device in FIG. 11 by using a cross section taken along line XII-XII in FIG. 11.

FIG. 11 is a perspective view illustrating a main unit of the medical device 300 according to the third embodiment. FIG. 12 is a perspective view illustrating the main unit of the medical device 300 in FIG. 11 by using a cross section taken along line XII-XII in FIG. 11.

The accommodation unit 310 can include the first cylinder 311, the second cylinder 312, a flat member 313, and a fixing member 314. The first cylinder 311 and the second cylinder 312 respectively have a cylindrical shape, and are joined to each other in a state where both of these are adjacent to each other along the axial direction. The flat member 313 is arranged inward from the first cylinder 311 and the second cylinder 312. The accommodation unit 310 can include a distal opening portion 310a on the distal side (upstream side along the axial direction) of the first cylinder 311 and the flat member 313. The accommodation unit 310 can include a proximal opening portion 310c on the further downstream side along the axial direction from the first cylinder 311. The accommodation unit 310 can include a lumen 310b for accommodating a capturing target, inward from the flat member 313. The accommodation unit 310 can be configured to exclude the flat member 313. In this case, the accommodation unit 310 integrally can include the lumen 310b inward from the first cylinder 311 and the second cylinder 312.

The first cylinder 311 is formed in a cylindrical shape. In the first cylinder 311, an inner peripheral surface excluding a distal portion has a screw groove 311d formed thereon. The screw groove 311d is screwed to a screw thread 312e of the second cylinder 312. The first cylinder 311 has a screw groove 311g formed from the outside to the inside of a side surface on the proximal side. The fixing member 314 is attached to the screw groove 311g.

If the first cylinder 311 is rotated to the second cylinder 312 in the clockwise direction, the first cylinder 311 is moved very close to the distal side of the second cylinder 312, thereby shortening a distance between the distal opening portion 310a of the first cylinder 311 and the distal opening portion 121a of the second cylinder 312. In a state illustrated in FIG. 12, the distance between the distal opening portion 310a of the first cylinder 311 and the distal opening portion 121a of the second cylinder 312 is in the most shortened state. In accordance with an exemplary embodiment, if the first cylinder 311 is rotated to the second cylinder 312 in the counterclockwise direction, the first cylinder 311 is moved separately from the distal side of the second cylinder 312, thereby lengthening the distance between the distal opening portion 310a of the first cylinder 311 and the distal opening portion 121a of the second cylinder 312. The first cylinder 311 is configured to include the same material as that of the first cylinder 311.

The second cylinder 312 is configured by deforming the second cylinder 121 of the impeller holding unit 120, and is arranged in place of the second cylinder 121. The second cylinder 312 corresponds to one in which the screw thread 312e is formed on an outer peripheral surface excluding a proximal portion of the second cylinder 121. The screw thread 312e is screwed to the screw groove 311d of the first cylinder 311. Specifications excluding the screw thread 312e of the second cylinder 312 are the same as specifications of the second cylinder 121.

The flat member 313 has a tubular shape along the axial direction in which the fluid flows, and is flexible. The flat member 313 is configured so that the inner surface of the lumen 310b of the accommodation unit 310 is smooth as a whole. The flat member 313 is formed so that the thickness is much thinner compared to the diameter. In the flat member 313, the distal portion is joined to the distal side of the first cylinder 311, and the proximal portion is joined to a portion having the proximal opening portion 121c arranged in the second cylinder 312. The flat member 313 is provided with flexibility so as to maintain a smooth state even in a state where the distal opening portion 310a of the first cylinder 311 moves closest to or farthest away from the distal opening portion 121a of the second cylinder 312.

The first cylinder 311 is screwed to the second cylinder 312, thereby causing the fixing member 314 to fix the lumen 310b through the entire length (distance between the distal opening portion 310a of the first cylinder 311 and the distal opening portion 121a of the second cylinder 312). The fixing member 314 is formed in a circular shape in which the distal portion has a set screw shape and the proximal portion is rotatable using a fingertip. The fixing member 314 is attached to the screw groove 311g of the first cylinder 311. If the fixing member 314 is rotated in the clockwise direction, the distal portion protrudes from the inner surface of the first cylinder 311, and presses the second cylinder 312, thereby fixing respective positions of the first cylinder 311 and the second cylinder 312 to each other. If the fixing member 314 is rotated in the counterclockwise direction, the distal portion is separated from the inner surface of the first cylinder 311, and no longer presses the second cylinder 312, thereby enabling the respective positions of the first cylinder 311 and the second cylinder 312 to be adjusted.

The fixing member 314 has been described as an example in which the fixing member 314 is configured to include a screw. However, various configurations can be adopted such as a configuration including a pin and a hole corresponding to the pin, a slide-type configuration including a convex portion and a concave portion corresponding to the convex portion. By appropriately configuring the fixing member, the first cylinder 311 and the second cylinder 312 can be joined to each other at various positions.

As described above, according to the medical device 300 of the third embodiment, the following configurations provide an operation effect.

According to the medical device 300, the deformable section can include the first deformable member (first cylinder 311) and the second deformable member (second cylinder 312). The first cylinder 311 is formed in a tubular shape along the axial direction in which the fluid flows. The second cylinder 312 is arranged adjacent to the first cylinder 311 in the axial direction, is formed in a cylindrical shape along the axial direction, and is configured to be joinable to the first cylinder 311. According to this configuration, the medical device 300 can adjust the entire length of the lumen 310b by using the first cylinder 311 and the second cylinder 312 which are joined to each other and which can change the entire length, and enables the inner surface of the lumen 310b to be flat as a whole before and after deformation. That is, the medical device 300 can maintain a sufficient suction force in each state before and after the deformation of the lumen 310b. Therefore, the medical device 300 can sufficiently capture a capturing target even if the lumen 310b is deformed. Furthermore, according to this configuration, the entire length of the lumen 310b can be accurately adjusted by using the first cylinder 311 and the second cylinder 312.

Furthermore, according to the medical device 300, the accommodation unit 310 can include the fixing member 314, which suppresses mobility of the deformable section. According to this configuration, after the entire length of the lumen 310b optionally adjusts, the medical device 300 can fix the entire length. Therefore, for example, even if the medical device 300 receives pressure when being introduced into the living body, the medical device 300 can maintain the entire length of the lumen 310b so as to be constant.

Furthermore, according to the medical device 300, the accommodation unit 310 can include the flat member 313 which is located between the deformable section and the lumen 310b, in which the inner surface is configured to be flat as a whole, and which covers at least a portion of the lumen 310b. According to this configuration, the medical device 300 enables the inner surface of the lumen 310b including the joined portion between the first cylinder 311 and the second cylinder 312 to be flat as a whole before and after the deformation.

Furthermore, according to the medical device 300, the flat member 313 is flexible. According to this configuration, the flat member 313 expands or contracts in accordance with the deformation of the lumen 310b. Therefore, the medical device 300 enables the inner surface of the lumen 310b to be uniformly flat as a whole before and after the deformation, without depending on the length along the axial direction of the lumen 310b.

Hitherto, the medical device according to the present disclosure has been described with reference to the multiple embodiments and modification examples. However, the present disclosure can be appropriately modified, based on the content disclosed in Claims.

For example, the medical device deforms the lumen, thereby enabling the outer shape of the accommodation unit to be deformed. Accordingly, the medical device can adjust the outer shape of the accommodation unit in accordance with various shapes inside the living body.

In addition, according to the medical device 100, if a cavity is formed inside the expandable member and a medium (gas or fluid) is introduced into or extracted from the cavity, an operator can deform the lumen 110b of the accommodation unit 110 inside the living body by operating the hand operation unit 150. For example, based on the operation of the operator, the lumen 110b can be lengthened in the axial direction by injecting compressed air into the cavity of the expandable member, or the lumen 110b can be shortened in the axial direction by aspirating the compressed air from the cavity of the expandable member.

In addition, the medical device is not limited to a form in which the medical device is introduced into the urinary duct 630 so as to capture and remove a capturing target. The medical device can be introduced into other sites inside the living body so as to capture and remove a capturing target. For example, other sites inside the living body correspond to the renal pelvis and renal calyx 640.

In addition, the flat member 313 described in the medical device according to the third embodiment can also be applied to each medical device according to the first embodiment or the second embodiment.

The detailed description above describes a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
an accommodation unit that includes a lumen which accommodates a capturing target present inside a living body, in which a shape of at least a portion on a distal side is expandable enabling the lumen of the accommodation unit to be increased or decreased in volume, wherein the accommodation unit includes an expandable section which is expandable along an axial direction in which the fluid flows, the expandable section having a contracted state and an expanded state, the contracted state having a length in the axial direction that is less than a diameter of the accommodation unit, and the expanded state having a length in the axial direction that is longer than the length in the axial direction of the contracted state, and wherein an inner surface of the at least the portion on the distal side before and after expansion is configured to be flat as a whole, a distal opening portion and a proximal opening portion which respectively communicate with the lumen, and a filter for capturing at least one or more of the capturing targets;

an impeller holding unit that includes an impeller which causes a fluid to flow from the distal opening portion toward the proximal opening portion inside the living body so as to allow the lumen to aspirate the capturing target together with the fluid;

an introduction unit configured to be used by an operator in order to introduce the accommodation unit and the impeller holding unit into the living body; and a hand operation unit configured to be operated by the operator in order to adjust a position of the first cylinder introduced in the living body and/or in order to rotate the impeller.

2. The medical device according to claim 1, wherein the expandable section includes an expandable member which has a tubular shape along the axial direction in which the fluid flows, and at least a portion of which is formed in a bellows shape so as to be expandable.

3. The medical device according to claim 1, wherein the expandable section includes a bending member which has a tubular shape along the axial direction in which the fluid flows, and at least a portion of which is flexible so as to be bendable, and a winding member which is wound in a spiral shape along the axial direction in which the fluid flows, radially outward or inward from the bending member.

4. The medical device according to claim 1, wherein the expandable section includes a first deformable member, which has a tubular shape along the axial direction in which the fluid flows, and a second deformable member, which is arranged adjacent to the first deformable member in the axial direction, which has a tubular shape along the axial direction, and which can be joined to the first deformable member.

5. The medical device according to claim 1, wherein the accommodation unit includes a fixing member which suppresses mobility of the expandable section.

6. The medical device according to claim 1, wherein the accommodation unit includes a flat member which is located between the expandable section and the lumen, whose inner surface is configured to be flat as a whole, and which covers at least a portion of the lumen.

7. The medical device according to claim 6, wherein the flat member is elastic.

8. A method for capturing a target present in a living body, the method comprising:
inserting an accommodation unit and an impeller holding unit into the living body with an introduction unit operated by an operator, the accommodation unit including a lumen which accommodates a capturing target present inside the living body, in which a shape of at least a portion on a distal side is expandable enabling the lumen of the accommodation unit to be increased or decreased in volume, wherein the accommodation unit includes an expandable section which is expandable along an axial direction in which the fluid flows, the expandable section having a contracted state and an expanded state, the contracted state having a length in the axial direction that is less than a diameter of the accommodation unit, and the expanded state having a length in the axial direction that is longer than the length in the axial direction of the contracted state, and wherein an inner surface of the at least the portion on the distal side before and after expansion is configured to be flat as a whole, a distal opening portion and a proximal opening portion which respectively communicate with the lumen, and a filter for capturing at least one or more of the capturing targets;

causing a fluid to flow with the impeller holding unit, the impeller holding unit including an impeller which causes the fluid to flow from the distal opening portion toward the proximal opening portion inside the living body so as to allow the lumen to aspirate the capturing target together with the fluid; and adjusting a position of the first cylinder introduced in the living body and/or rotating the impeller with a hand operation unit operated by the operator.

9. The method according to claim 8,
wherein the expandable section includes an expandable member which has a tubular shape along the axial direction in which the fluid flows, and at least a portion of which is formed in a bellows shape so as to be expandable.

10. The method according to claim 8,
wherein the expandable section includes a bending member which has a tubular shape along the axial direction in which the fluid flows, and at least a portion of which is flexible so as to be bendable, and a winding member which is wound in a spiral shape along the axial direction in which the fluid flows, radially outward or inward from the bending member.

11. The method according to claim 8,
wherein the expandable section includes a first deformable member, which has a tubular shape along the axial direction in which the fluid flows, and a second deformable member, which is arranged adjacent to the first deformable member in the axial direction, which has a tubular shape along the axial direction, and which can be joined to the first deformable member.

12. The method according to claim 8, comprising:
suppressing mobility of the expandable section with a fixing member.

13. The method according to claim 8,
locating a flat member between the expandable section and the lumen, and wherein an inner surface of the flat member is configured to be flat as a whole and covers at least a portion of the lumen.

14. The method according to claim 13,
wherein the flat member is elastic.

15. The medical device according to claim 1,
wherein the lumen is cylindrical.

16. A medical device for capturing a target present inside a living body, the medical device comprising:
an accommodation unit having a lumen, the accommodation unit including a first cylinder, an expandable member, and a filter for capturing at least one or more of the capturing targets, the expandable member having a contracted state and an expanded state, the contracted state having a length in an axial direction that is less than a diameter of the accommodation unit, and the expanded state having a length in the axial direction that is longer than the length in the axial direction of the contracted state, the first cylinder and the expandable member having a cylindrical shape and joined together in a state where the first cylinder and the expandable member are adjacent to each other along an axial direction, and wherein an inner surface of the expandable member and the first cylinder before and after expansion of the expandable member is configured to be smooth as a whole, and a distal opening portion and a proximal opening portion which respectively communicate with the lumen;

an impeller holding unit that includes an impeller which causes a fluid to flow from the distal opening portion toward the proximal opening portion inside the living body so as to allow the lumen to aspirate the capturing target together with the fluid;

an introduction unit configured to be used by an operator in order to introduce the accommodation unit and the impeller holding unit into the living body; and a hand operation unit configured to be operated by the operator in order to adjust a position of the first cylinder introduced in the living body and/or in order to rotate the impeller.

17. The medical device according to claim 16,
wherein the expandable member has a tubular shape along the axial direction in which the fluid flows, and at least a portion of the expandable member is formed in a bellows shape so as to be expandable.

* * * * *